United States Patent
An et al.

(10) Patent No.: US 10,342,236 B2
(45) Date of Patent: Jul. 9, 2019

(54) NATURAL BROAD-SPECTRUM PRESERVATIVE COMPOSITION CONTAINING CITRUS GRANDIS FRUIT EXTRACT AND ITS USE

(71) Applicant: Spec-Chem Industry Inc., Nanjing, Jiangsu (CN)

(72) Inventors: Qinglian An, Jiangsu (CN); Jiansheng Zha, Jiangsu (CN); Jinrong Xu, Jiangsu (CN)

(73) Assignee: SPEC-CHEM INDUSTRY INC., Nanjing, Jiangsu (CN)

(*) Notice: Subject to any disclaimer, the term of this patent is extended or adjusted under 35 U.S.C. 154(b) by 0 days.

(21) Appl. No.: 15/739,523

(22) PCT Filed: Feb. 3, 2016

(86) PCT No.: PCT/CN2016/073395
§ 371 (c)(1),
(2) Date: Dec. 22, 2017

(87) PCT Pub. No.: WO2017/092177
PCT Pub. Date: Jun. 8, 2017

(65) Prior Publication Data
US 2018/0177197 A1 Jun. 28, 2018

(30) Foreign Application Priority Data
Dec. 3, 2015 (CN) .......................... 2015 1 0875346

(51) Int. Cl.
*A61K 8/34* (2006.01)
*A61K 8/9789* (2017.01)
*A61Q 1/14* (2006.01)
*A61Q 19/10* (2006.01)
*A01N 65/00* (2009.01)
*A61K 8/42* (2006.01)
*A61Q 19/00* (2006.01)
*A01N 31/02* (2006.01)
*A01N 31/04* (2006.01)
*A61K 8/96* (2006.01)
*A61Q 5/02* (2006.01)
*A61Q 5/12* (2006.01)

(52) U.S. Cl.
CPC ............. *A01N 65/00* (2013.01); *A01N 31/02* (2013.01); *A01N 31/04* (2013.01); *A61K 8/345* (2013.01); *A61K 8/347* (2013.01); *A61K 8/42* (2013.01); *A61K 8/96* (2013.01); *A61K 8/9789* (2017.08); *A61Q 19/00* (2013.01); *A61K 2800/10* (2013.01); *A61K 2800/524* (2013.01); *A61Q 1/14* (2013.01); *A61Q 5/02* (2013.01); *A61Q 5/12* (2013.01); *A61Q 19/10* (2013.01)

(58) Field of Classification Search
None
See application file for complete search history.

(56) References Cited

U.S. PATENT DOCUMENTS
2012/0201902 A1 8/2012 Modak et al.

FOREIGN PATENT DOCUMENTS
CN 102920612 2/2013
EP 1543812 A1 * 6/2005 ............... A61K 8/31

OTHER PUBLICATIONS

EP 1543812 Google translation, pp. 1-7 [(on-line website: https://patents.google.com/patent/EP1543812A1/en, access date: Jan. 17, 2019)]. (Year: 2005).*

CN102920612 EPO translation, pp. 1-15 [(obtained from on-line website:http://translationportal.epo.org/emtp/translate/?ACTION=description-retrieval&COUNTRY=CN&ENGINE=google&FORMAT=docdb&KIND=A&Locale=en_EP&NUMBER=102920612&OPS=ops.epo.org/3.2&SRCLANG=zh&TRGLANG=en, access date: Jan. 17, 2019)]. (Year: 2013).*

Written Opinion and International Search Report for International patent application No. PCT/CN2016/073395 dated Sep. 7, 2016; 9 pages.

* cited by examiner

*Primary Examiner* — Ernst V Arnold
*Assistant Examiner* — Kyung S Chang
(74) *Attorney, Agent, or Firm* — Rankin, Hill & Clark LLP

(57) ABSTRACT

The present invention discloses a natural broad-spectrum preservative composition containing a *citrus grandis* fruit extract and its use. The composition mainly comprises a *citrus grandis* fruit extract, a hydroximic acid, an aromatic alcohol, and one or more polyols. The preservative composition uses a natural *citrus grandis* fruit extract as a main raw material, which is combined with a hydroxamic acid having a good inhibitory effect on fungi and an aromatic alcohol having a good inhibitory effect on bacteria dissolved in an improved functional solvent, has the characteristics of low irritation and high safety, and not only provides an excellent broad-spectrum bacteriostatic effect, but also improves the performance and values of the product due to the good oxidation resistance of the *citrus grandis* fruit extract.

12 Claims, No Drawings

NATURAL BROAD-SPECTRUM PRESERVATIVE COMPOSITION CONTAINING CITRUS GRANDIS FRUIT EXTRACT AND ITS USE

TECHNICAL FIELD

The present invention relates to the field of cosmetic preservatives, and more particularly to a natural broad-spectrum preservative composition containing a *citrus grandis* fruit extract and its use.

BACKGROUND ART

Cosmetics contain a lot of nutrients beneficial to human skin growth, and these nutrients are also substances which a variety of microorganisms enjoy. The presence of a large number of microorganisms results in cosmetic deterioration and generates toxins harmful to human body. Therefore, in order to improve the shelf life of cosmetics, preservatives are often added in cosmetic formulations. Traditional preservatives such as formaldehyde and formaldehyde releaser, Bronopol, organic halogens and paraben esters themselves may generate carcinogenic and allergenic substances in use, and should be avoided in cosmetic formulations. In recent years, looking for broad-spectrum, mild and effective preservative formulations is the goal of most cosmetics companies, and the synergistic effect of compounded cosmetic preservatives is the research direction of most cosmetics companies.

On the other hand, with the improvement of consumers' cognition, the concepts of "natural ingredients" and "zero additive" in cosmetics have drawn more and more attention. People began to look for natural raw materials with a preservative effect for compounding, and the addition of preservative raw materials restricted in the current hygienic standard for cosmetics is avoided, so that compounded products often have a greatly reduced preservative effect, and due to the complexity of the ingredients added, their solubility and preservative effectiveness are greatly challenged.

SUMMARY OF THE INVENTION

Objectives of the invention: an objective of the present invention is to provide a broad-spectrum preservative composition which contains natural preservative components and has an excellent preservative effect on both bacteria and fungi, another objective of the present invention is to provide the use of the composition in the field of cosmetics, and a further objective of the present invention is to provide a cosmetic product containing the broad-spectrum preservative composition.

Technical solution: in order to achieve the above-mentioned objectives, the natural broad-spectrum preservative composition containing a *citrus grandis* fruit extract of the present invention comprises, in mass percentage, 40-70% of a *citrus grandis* fruit extract, 2-11% of octanohydroxamic acid, 6-18% of an aromatic alcohol, and 10-45% of a polyol.

The *citrus grandis* fruit extract (or Grapefruit Seed Extract, abbreviated as GSE) of the present invention has an INCI name of "*Citrus Grandis* Extract", CAS: 90045-43-5, which is a product obtained from cheap residues from the production of grapefruit juice as raw materials after a simple processing process, these residues are mainly seeds, pulp and peel, and the process mainly includes drying, squeezing and extraction, drying at 150-204° C. and then milling and cooling. Common products are in a powder or solution form and are directly available on the market. It should be noted that: the mass percentage of the *citrus grandis* fruit extract of the present invention represents GSE active components in the product in the form of a GSE powder or GSE solution, but not all of the mixture or solution. Grapefruit (*Citrus paradisi* Macf) is from Florida, USA, and is a Rutaceae plant containing significant amounts of pomelo peel essence oil, pectin and total flavonoids. The *citrus grandis* fruit extract contains not less than 50% by mass of D-limonene, not less than 10% by mass of β-myrcene and not less than 1% by mass of β-pinene, and has a strong reducibility and antioxidant activity. In the present invention, the *citrus grandis* fruit extract not only has a good inhibitory activity against *Escherichia coli, Staphylococcus aureus* and *Salmonella*, but also has a good inhibitory effect on fungi, and is mainly used as a natural bacteriostatic component in the composition of the present invention. More importantly, adding GSE as a preservative to cosmetics can increase the overall antioxidant capacity to prevent the oxidation of other components of the cosmetics, and since the GSE of the present invention has a higher content, the artificial antioxidants added in the cosmetics can be replaced through a reasonable preservative formulation.

The aromatic alcohol is any one of benzyl alcohol, phenethyl alcohol or phenoxyethanol, which is mainly used for inhibiting bacteria in the present invention. Benzyl alcohol, CAS No. 100-51-6, also known as phenylcarbinol, is a colorless and transparent viscous liquid with a weak aromatic odor, and is mainly used in the fields of food flavors and daily use chemical essence, as a restricted preservative in *Hygienic Standard for Cosmetics* in our country, with its amount not exceeding 1% of the mass of cosmetics. Phenethyl alcohol, CAS No. 60-12-8, has two isomeric alcohols containing a benzene ring. The present invention uses β-phenyl ethanol, and preferably the addition amount thereof is 8-15%. Phenethyl alcohol was first found in natural plants such as apples, almonds, bananas, peaches, pears, strawberries, cocoa, and honey, and was commonly used in honey, bread, apples, rose fragrance, etc. Later, researchers found that phenylethyl alcohol has a certain bacteriostatic effect, and is widely used in the fields of cosmetics and foodstuffs as a non-polluting bacteriostatic agent. Phenethyl alcohol has a good biodegradability, does not irritate skin and is more chemically stable than benzyl alcohol, and thus phenethyl alcohol is preferred.

The polyol includes, but is not limited to, glycerol, 1,2-propanediol, 1,3-propanediol, 1,2-butanediol, 1,2-pentanediol, 1,5-pentanediol, 3-[2-(ethylhexyl)oxyl]-1,2-propanediol, or a combination of any one or more thereof. Polyols are good solvents, many of which have a good water retention, wherein 1,3-propanediol and 1,2-butanediol are solvents having a certain bacteriostatic effect.

As a further optimization of the present invention, the polyol is glycerol, 1,3-propanediol and 3-[2-(ethylhexyl)oxyl]-1,2-propanediol, wherein 3-[2-(ethylhexyl)oxyl]-1,2-propanediol accounts for 10-40% of the mass of the polyol. 3-[2-(ethylhexyl)oxyl]-1,2-propandiol as a preservative component has both hydrophobic and hydrophilic groups, which can effectively enhance the moisturizing capacity of cosmetics, and also has a certain emulsifying ability, which is conducive to the mixing of various formulations of cosmetics. Cosmetics formulated with preservatives containing 3-[2-(ethylhexyl)oxyl]-1,2-propandiol can regulate the aqueous and oil phases well. It is noteworthy that the present invention provides a polyol combination method, and therefore not only GSE and octanohydroxamic acid are dissolved in a homogeneous system, but also the cooperation of 3-[2-(ethylhexyl)oxyl]-1,2-propandiol and the aromatic alcohol can significantly improve the inhibitory effect on bacteria.

The octanohydroxamic acid is a hydroxamic acid which is mainly used for inhibiting fungi in the composition of the present invention. Octanohydroxamic acid, CAS No: 7377-03-9, is the only organic acid that remains an unionized state from acidic to neutral and has a very strong inhibitory effect on molds. CHA has an efficient and selective chelation effect on $Fe^{2+}$ and $Fe^{3+}$, limiting the growth of molds in an iron ion-limited environment. In the present invention, the addition amount of octanohydroxamic acid is 2-11%, preferably 4.5-7.5%, and when the preservative is added in an amount of more than 0.8% and is combined with the *citrus grandis* fruit extract and aromatic alcohol, a very excellent broad-spectrum antibacterial effect can be achieved.

As a preferred solution of the present invention, the natural broad-spectrum preservative composition containing a *citrus grandis* fruit extract comprises, in mass percentage, 50-60% of a *citrus grandis* fruit extract, 4.5-7.5% of octanohydroxamic acid, 8-15% of phenylethyl alcohol, 10-25% of glycerol, 2-10% of 3-[2-(ethylhexyl)oxyl]-1,2-propanediol, and 0-10% of 1,3-propanediol.

For another preferred solution, the natural broad-spectrum preservative composition containing a *citrus grandis* fruit extract comprises, in mass percentage, 50-60% of a *citrus grandis* fruit extract, 4.5-7.5% of octanohydroxamic acid, 8-15% of phenylethyl alcohol, 10-20% of glycerol, 1-5% of 3-[2-(ethylhexyl)oxyl]-1,2-propanediol, and 5-15% of 1,2-propanediol.

Nowadays, the concept of "zero additive" is very much concerned in the field of cosmetics, that is, cosmetics do not contain any preservatives, and zero-additive cosmetics are very attractive to consumers and increase the sense of safety for consumers. The substances used in the composition of the present invention all have a certain preservative effect and are not in the list of restricted preservatives in our country; and at the same time, the preservative composition also contains many natural components, for example, GSE is extracted from grapefruit, and 1,3-propanediol is obtained by a bio-based propylene glycol production process, such as by fermenting of corn starch (such as corn), and is a safe, reliable, natural and harmless solvent. Through the mutual cooperation and combination with the solvent, a preservative composition having an excellent inhibitory effect on both bacteria and fungi and having a certain oxidation resistance is obtained.

The mass percentage of the preservative composition added to the cosmetic formulation is 0.5-1.5%, preferably 1.1-1.5%. When the addition amount reaches 1.5%, the content of GSE active component in cosmetics is close to 1%, and the anti-oxidation effect of GSE at this content has basically satisfied most cosmetics; at the same time, octanohydroxamic acid and phenethyl alcohol can be completely dissolved in the polyol solution at a lower content, and function to inhibit bacteria and fungi together with GSE.

The preservative composition of the present invention has a pH value in the usage range of 2 to 8 and can be used for formulating a hair conditioner, cleansing oil, anti-allergic moisturizing cream, shampoo and the like; and cosmetics formulated with this preservative composition may be in various forms of solutions, gels, lotions and creams. After the addition of the preservative composition, heating at 90° C. for less than 2 h and heating at 60° C. for less than 6 h. When the cosmetic is a surfactant system-based cosmetic, the preservative should be added below 60° C. In the use of the preservative composition of the present invention, deionized water should be used, an appropriate amount of chelating agent (EDTA-2Na) should be added, and copper ions and iron ions should be avoided as far as possible to prevent color change phenomenon.

The preservative composition of the present invention uses the natural *citrus grandis* fruit extract as a main raw material, which is combined with a hydroxamic acid having a good inhibitory effect on fungi and an aromatic alcohol having a good inhibitory effect on bacteria dissolved in an improved functional polyol solvent, has the characteristics of low irritation and high safety, and not only provides an excellent broad-spectrum bacteriostatic effect, but also improves the performance and values of the product due to the good oxidation resistance of the *citrus grandis* fruit extract. The composition can effectively inhibit Gram-negative bacteria, positive bacteria, yeasts and molds, and has a good compatibility with most cosmetic raw materials; and its bacteriostatic capacity is not affected by pH, nonionic surfactants, light heating, packaging and chelating agents in cosmetics.

DETAILED DESCRIPTION OF THE EMBODIMENTS

The present invention is further illustrated by the following specific embodiments. It should be noted that for a person skilled in the art, some variations and improvements can also be made under the premise of not departing from the principle of the present invention, and these variations and improvements are also considered to be within the protection scope of the present invention. It should be noted that the following embodiments, unless otherwise specified, are based on mass percentage.

A natural broad-spectrum preservative composition containing *citrus grandis* fruit extract comprises, in mass percentage, 40-70% a *citrus grandis* fruit extract,
2-11% octanohydroxamic acid,
6-18% an aromatic alcohol, and
10-45% a polyol.

The *citrus grandis* fruit extract is obtained by subjecting the residues from the production of grapefruit juice to drying, squeezing and extraction, drying at 150-204° C. and then milling and cooling. It contains not less than 50% by mass of D-limonene, not less than 10% by mass of β-myrcene and not less than 1% by mass of β-pinene, and has a strong reducibility and antioxidant activity.

The polyol includes glycerol, 1,2-propanediol, 1,3-propanediol, 1,2-butanediol, 1,2-pentanediol, 1,5-pentanediol, 3-[2-(ethylhexyl)oxyl]-1,2-propanediol, or a combination of any one or more thereof. When 3-[2-(ethylhexyl)oxyl]-1,2-propandiol is contained, the bacteriostatic effect of the bacteriostatic components can be remarkably improved, and the aqueous phase-oil phase balance of the composition can be improved. The addition amount of 3-[2-(ethylhexyl)oxyl]-1,2-propandiol accounts for 10-40% of the mass of the polyol.

The preservative composition has a pH value in the usage range of 2 to 8 and can be used for formulating a hair conditioner, cleansing oil, anti-allergic moisturizing cream, shampoo and the like; cosmetics formulated with this preservative composition may be in various forms of solutions, gels, lotions and creams; and an addition amount of 0.5-1.5% by mass percentage can reach an excellent bacteriostatic effect.

In the use of the preservative composition, after the addition thereof, heating at 90° C. for less than 2 h and heating at 60° C. for less than 6 h. When the cosmetic product is a surfactant system-based cosmetic, the preservative should be added below 60° C. In the use of the preservative composition of the present invention, deionized water should be used, an appropriate amount of chelating agent (EDTA-2Na) should be added, and copper ions and iron ions should be avoided as far as possible to prevent color change phenomenon.

Table 1 lists several specific embodiments of the preservative composition of the present invention:

TABLE 1

Preservative composition group and embodiments

| | Citrus grandis fruit extract % | Octanohydroxamic acid % | Aromatic alcohol | Polyol |
|---|---|---|---|---|
| Embodiment 1 | 40 | 5 | 10% benzyl alcohol | 25% glycerol 10% 1,3-propanediol 10% 3-[2-(ethylhexyl)oxyl]-1,2-propandiol |
| Embodiment 2 | 45 | 11 | 18% phenoxyethanol | 16% glycerol 5% 1,3-propanediol 5% 3-[2-(ethylhexyl)oxyl]-1,2-propandiol |
| Embodiment 3 | 55 | 2 | 6% phenethyl alcohol | 18% glycerol 19% 1,3-propanediol |
| Embodiment 4 | 55 | 5.5 | 11.5% phenethyl alcohol | 18% glycerol 10% 1,3-propanediol |
| Embodiment 5 | 55 | 8 | 14% phenethyl alcohol | 18% glycerol 5% 1,3-propanediol |
| Embodiment 6 | 55 | 10 | 17% phenethyl alcohol | 18% glycerol |
| Embodiment 7 | 55 | 5.5 | 11.5% phenethyl alcohol | 28% glycerol |
| Embodiment 8 | 55 | 5.5 | 11.5% phenethyl alcohol | 16% glycerol 6% 1,3-propanediol 6% 3-[2-(ethylhexyl)oxyl]-1,2-propandiol |
| Embodiment 9 | 70 | 2 | 6% phenethyl alcohol | 22% glycerol |
| Embodiment 10 | 70 | 5.5 | 11.5% phenethyl alcohol | 13% glycerol |

Embodiment 11 a Hair Conditioner Containing a Natural Preservative Composition Preservative composition A used the formulation in Embodiment 5.

TABLE 2

Formulation of a hair conditioner containing a natural preservative composition

| | Name of raw materials | Amount wt % | Supplier |
|---|---|---|---|
| Oil phase | Octadecanol | 6.0 | Cognis |
| | Docosyltrimethylammonium chloride | 1.0 | Shanghai Oli Co., Ltd. |
| | Cyclic methylsiloxane (and) hydroxyl-terminated polydimethylsiloxane (TC1214) | 2.5 | Guangzhou Tinci Co., Ltd. |

TABLE 2-continued

Formulation of a hair conditioner containing a natural preservative composition

| | Name of raw materials | Amount wt % | Supplier |
|---|---|---|---|
| | Dimethicone (100 cst) | 1.5 | Dow Corning |
| | Transparent silicone oil (TC1233) | 1.5 | Guangzhou Tinci Co., Ltd. |
| Aqueous phase | Glycerol | 3.0 | Nature |
| | HEC (hydroxyethyl cellulose) | 0.5 | Akzo |
| | Cationic hydroxyethyl cellulose | 0.3 | |
| | Deionized water | To 100 | |
| Preservative composition A | | 1.2 | SC |
| Essence | | q.s. | |

Operation Process:

1. the components in the oil phase components other than TC-1214 and TC-1233 were heated to 75° C. for ready use;

2. the cationic hydroxyethyl cellulose and HEC were added to an aqueous phase pot, stirred and dispersed evenly, and heated to 70-75° C.;

3. when the aqueous phase was heated to 70-75° C., the oil phase obtained in step 1 was added to an emulsification pot under stirring; and after the addition of the oil phase was finished, homogeneous emulsification was started;

4. the temperature was decreased to 55-60° C. by cooling, at this time sampling detection showed a pH value of 4.65, and a uniform mixture of TC-1214 and TC-1233 and a preservative (PrzvFree® plus) were added to the emulsification pot and can be homogenized for 3 min; and 5. the temperature was continued to decrease to 40-45° C., and P.O. and essence pre-dispersed with deionized water were added and stirred for 10-15 min, and then the materials were discharged.

Embodiment 12 a Cleansing Oil Containing a Natural Preservative Composition

Preservative composition B was formulated using the composition of Embodiment 4.

TABLE 3

Formulation of a cleansing oil containing a natural preservative composition

| Phase | Name of raw materials | Amount Wt % | Supplier |
|---|---|---|---|
| Phase A | Isooctyl palmitate | 30.0 | Kunshan Shuangyou Co., Ltd. |
| | PEG-7 olive oil ester | 18.0 | B&T |
| | C12-15 benzoate | 45.0 | Taiwan Patech Co., Ltd. |
| | PEG-7 cocoglyceride | 5.0 | Cognis |
| Phase B | Preservative composition B | 0.9 | SC |
| | Essence | q.s. | |

Operation Process:

1. the components in phase A were sequentially mixed, stirred and dissolved until complete transparency was achieved; and 2. the preservative (PrzvFree® plus) and essence in phase B were sequentially added with constant stirring, after adding, they were stirred until complete transparency was achieved.

The formulation was pure oil, of which the pH value was unable to measure, and this scheme showed that the preservative can be used in anhydrous cosmetics.

Embodiment 13 an Anti-Allergic Moisturizing Cream Containing a Natural Preservative Composition Preservative composition C was formulated using the composition of Embodiment 8.

TABLE 4

Formulation of an anti-allergic moisturizing cream containing a natural preservative composition

| Classi-fication | Name of raw materials | Amount Wt % | Supplier |
|---|---|---|---|
| Phase A | GP200 (Ceteareth-20 (and) Ceteareth-10 (and) cetearyl alcohol) | 3.0 | Croda |
| | 1618 alcohol (cetearyl alcohol) | 3.0 | Cognis |
| | Monoglyceride (glyceryl monostearate) | 2.8 | Cognis |
| | White oil | 2.0 | Hangzhou Refinery |
| | Isopropyl myristate | 2.0 | Cognis |
| | Dioctyl carbonate | 2.0 | Cognis |
| | Polydimethylsiloxane | 0.5 | Dow Corning |
| | CM040 (cyclopentasiloxane) | 1.5 | Germany Wacker Company |
| | α-Dragosantol | 0.2 | |
| | 2,6-di-tert-butyl-4-methylphenol | 0.04 | |
| Phase B | Glycerol | 5.0 | |
| | Xanthan gum | 0.05 | |
| | Allantoin | 0.2 | Kunshan Shuangyou Co., Ltd. |
| | Co-emulsifier HR-S$_1$ | 0.5 | Dandong Ankang Co., Ltd. |
| | Amino acid moisturizer NMF-50 | 0.5 | |
| | Deionized water | To 100 | |
| Phase C | Sodium hyaluronate (1%) | 1.5 | Shandong Freda Co., Ltd. |
| Phase D | Preservative composition C | 1.5 | |
| | Essence | q.s. | |

Operation Process:

1. the raw materials of phase A (oil phase) were accurately weighed, heated, stirred and dissolved with the temperature controlled at 80±2° C.; (Note: it was suggested that cyclopentasiloxane be added before the emulsification of oil and water phases);

2. phase B (aqueous phase): the glycerol and xanthan gum in phase B were pre-mixed and dispersed evenly, added to deionized water, and heated and stirred until completely dissolved; when about 90° C. was reached, heating was stopped; the other components of phase B were added and continued to be stirred until completely dissolved; and before emulsification, the temperature was controlled at about 85° C.;

3. the oil phase was first sucked into an emulsifying pot, the aqueous phase was sucked under constant stirring, and homogeneous emulsification was started for 15 min;

4. the temperature was decreased to 60° C., the stirring speed of scrapers was increased, and phase C was added; and then phase D was added at 48° C. and stirred evenly; and 5. after the temperature was decreased to 45-50° C., the paste was recovered, stirring was stopped, and the materials were discharged. Sampling detection showed a pH value of 6.50.

Embodiment 14 an Anti-Dandruff and Smoothing Shampoo Containing a Natural Preservative Composition Preservative composition D was formulated using the composition of Embodiment 8.

TABLE 5

Formulation of an anti-dandruff and smoothing shampoo containing a natural preservative composition

| Name of raw materials | Amount Wt % | Supplier |
|---|---|---|
| Deionized water | To 100 | |
| EDTA-2Na | 0.10 | |
| AESA (70%) (ammonium alcohol ether sulphate) | 8 | Zhejiang Zanyu Co., Ltd. |
| LSA (70%) (fatty alcohol ammonium sulfate) | 8 | Zhejiang Zanyu Co., Ltd. |
| TC-8025 (polyquaternium-10 (and) lauryl methyl gluceth-10 hydroxypropyldimonium chloride (and) water) | 5 | Guangzhou Tinci Co., Ltd. |
| C-14-S (cationic guar gum) | 0.15 | Guangzhou Tinci Co., Ltd. |
| Cetostearyl alcohol | 0.5 | Cognis |
| Pearling agent | 1.0 | Guangzhou Daoming Co., Ltd. |
| CMEA (coconut oil monoethanolamide) | 1 | Shanghai Goodway Co., Ltd. |
| TC-23 (di(hydrogenated tallow)benzoic acid amide) | 0.5 | Guangzhou Tinci Co., Ltd. |
| CAB-35 (cocamidopropyl betaine) | 5 | Guangzhou Tinci Co., Ltd. |
| TC-1352 (polydimethylsiloxane (and) laureth-23 (and) sodium laureth sulfate) | 2 | Guangzhou Tinci Co., Ltd. |
| Preservative composition D | 1.4 | SC |
| Citric acid | Appropriately adjusting the pH to 6.0-6.5 | |
| Essence | q.s. | |

Operation Process:

1. C-14-S was dispersed in deionized water to obtain a C-14-S solution;

2. TC-8025 was then added to the C-14-S solution, EDTA-2Na was then added to obtain a mixed solution, and the mixed solution was added to a pot;

3. AESA and LSA were then added to the pot, and heated to 75-80° C. and dissolved;

4. the pearling agent, CMEA, cetostearyl alcohol and TC-23 were then mixed and heated to 80° C., added to the pot under stirring, and mixed for 15-20 min;

5. the temperature was decreased to 50° C., and the TC-1352 emulsified silicone oil, CAB-35, preservative, and essence were sequentially added;

6. P.O. was dispersed in an appropriate amount of deionized water, and then added to the system; and 7. after uniform mixing, citric acid was used to adjust the pH to 6.0-6.5, and after being adjusted to be qualified, the materials were discharged.

Embodiment 15 a DHA Tanning Cream Containing a Natural Preservative Composition Preservative composition E was formulated by using the composition of Embodiment 8.

TABLE 6

Formulation of a DHA tanning cream containing a natural preservative composition

| Classification | Name of raw materials | Amount Wt % | Supplier |
|---|---|---|---|
| Phase A | Tego Care 150 (glyceryl stearate, Ceteareth-25 (and) Ceteth-20 (and) stearyl alcohol) | 8.0 | Degussa |
| | 1618 alcohol (cetearyl alcohol) | 1.0 | Cognis |
| | Eutanol G (octyldodecanol) | 2.0 | Cognis |
| | 26 white oil | 5.0 | Hangzhou Refinery |
| | GTCC (caprylic/capric triglyceride) | 2.0 | Cognis |
| | Dioctyl carbonate | 2.0 | Cognis |
| | DC200 (polydimethylsiloxane) | 0.5 | Dow Corning |
| | α-Dragosantol | 0.2 | |
| | 2,6-di-tert-butyl-4-methylphenol | 0.05 | |
| Phase B | Glycerol | 3.0 | |
| | Amino acid moisturizer NMF-50 | 1.0 | |
| | Deionized water | To 100 | |
| Phase C | Preservative composition E | 1.4 | |
| | Essence | q.s. | |
| Phase D | Dihydroxyacetone (DHA) | 6.0 | |
| | Deionized water | 12.0 | |

Operation Process:

1. the raw materials of phase A (oil phase) were accurately weighed, heated, stirred and dissolved with the temperature controlled at 80±2° C.;

2. phase B (aqueous phase): the raw materials of phase B were heated and stirred until completely dissolved; when about 90±2° C. was reached, heating was stopped; and before emulsification, the temperature was controlled at about 80±3° C.;

3. the oil phase was first sucked into an emulsifying pot, the aqueous phase was sucked under constant stirring, and homogeneous emulsification was started for 15 min;

4. the temperature was decreased to 48° C., the stirring speed of scrapers was increased, and phase C was added and continued to be stirred; and 5. after the temperature was decreased to 40° C., phase D was added and stirred evenly, sampling detection showed a pH value of 2.50, and the materials were discharged.

Embodiment 16 an Anti-Itch and Revitalizing Body Wash Containing a Natural Preservative Composition Preservative composition F was formulated by using the composition of Embodiment 8.

TABLE 7

Formulation of a DHA tanning cream containing a natural preservative composition

| Classification | Name of raw materials | Amount Wt % | Supplier |
|---|---|---|---|
| Phase A | EDTA-2Na | 0.05 | |
| | H₂O (deionized water) | To 100 | |
| | 250HHR (hydroxyethyl cellulose) | 0.8 | Aqualon |
| | KOH (potassium hydroxide) | 5.0 | UNID (Jiangsu) Chemical Co., Ltd |
| | Dodecanoic acid | 10 | Cognis |
| | Tetradecanoic acid | 6 | Cognis |
| | Octadecanoic acid | 4 | Cognis |
| | Pearling agent (ethylene glycol distearate) | 2.5 | Shanghai Oli Co., Ltd. |

TABLE 7-continued

Formulation of a DHA tanning cream containing a natural preservative composition

| Classification | Name of raw materials | Amount Wt % | Supplier |
|---|---|---|---|
| | BHT (2,6-di-t-butyl-4-methylphenol) | 0.02 | |
| | Shea butter | 0.2 | A&K |
| | Glycerol | 5 | |
| | CES (sodium coco alcohol ether carboxylate) | 8 | |
| | NMF-50 (amino acid moisturizer) | 0.5 | SC |
| Phase B | Preservative composition F | 1.3 | SC |
| | Essence (rose) | 0.3 | |

Operation Process:

1. 250HHR in phase A was added to weighed deionized water, heated, stirred and dissolved until transparency was achieved, then EDTA-2Na in phase A was added, the temperature was controlled at 80-85° C., and then KOH was added; after complete dissolution, the glycerol, dodecanoic acid, tetradecanoic acid and hexadecanoic acid in phase A were added; after complete dissolution, reaction under stirring while maintaining the temperature was performed for 40-50 min; then the pearling agent, BHT and CES in phase A were sequentially added and stirred for 20 min while maintaining the temperature; and shea butter and NMF-50 were added and stirred for 5 min, and cooling water was opened for cooling; and 2. after the temperature was decreased to 48° C., phase B was added and stirred for 15 min until uniformly dispersed and dissolved, and then sampling detection showed a pH value of 8.0.

Test Example 1 Dissolving Capacity Test

The invention compounds GSE, octanohydroxamic acid and an aromatic alcohol, and the first problem to be solved is the solubility problem. In this test, the dissolution abilities of the compositions of Embodiments 6-9 were evaluated at different temperatures by sensory evaluation, after the compositions were placed in a container and left to stand for 10 min, the sensory evaluation was performed, and the results were as follows:

TABLE 8

Dissolving capacity test

| | 25° C. | 4° C. | 0° C. |
|---|---|---|---|
| Embodiment 6 | Dissolved | Precipitation•less | Precipitation•more |
| Embodiment 7 | Dissolved | Dissolved | Precipitation•less |
| Embodiment 8 | Dissolved | Dissolved | Dissolved |
| Embodiment 9 | Dissolved | Dissolved | Precipitation•less |
| Embodiment 10 | Dissolved | Dissolved | Precipitation•less |

It can be seen from Table 8 that the factor greatly affecting the dissolving ability is mainly that the ratio of octanohydroxamic acid to aromatic alcohol; it is almost saturated when the content of GSE reaches 70%; and a too low content of the glycerol solvent also affected the dissolving ability of the whole components. As can be seen from the results between Embodiments 7 and 8, the addition of 6% 3-[2-(ethylhexyl)oxyl]-1,2-propandiol can better adjust the solvent structure and increase the dissolving capacity.

Test Example 2 Preservative Challenge Test

According to CTFA standard, the following preservative test was conducted. The test was carried out under the same initial concentration of strain using Embodiment 3, Embodiment 4, Embodiment 5, Embodiment 7 and Embodiment 8. The addition amount of the preservative was 1%. Statistics were taken at 2 weeks and 4 weeks to finally calculate the strain reduction amount.

TABLE 9

Preservative challenge Test-Comparison 1

| Test strain | Initial strain Concentration (CFU/ML) | Results (Log reduction value) (CFU/ML) | | | | | |
|---|---|---|---|---|---|---|---|
| | | Embodiment 3 | | Embodiment 4 | | Embodiment 5 | |
| | | 7 d | 28 d | 7 d | 28 d | 7 d | 28 d |
| Staphylococcus aureus | $5.40 \times 10^5$ | 2.79 | 5.73(N.1.) | 2.86 | 5.73(N.1.) | 3.03 | 5.73(N.1.) |
| Escherichia coli | $3.00 \times 10^5$ | 4.11 | 5.47(N.1.) | 4.30 | 5.47(N.1.) | 4.47 | 5.47(N.1.) |
| Pseudomonas aeruginosa | $5.90 \times 10^5$ | 4.22 | 5.77(N.1.) | 4.33 | 5.77(N.1.) | 4.35 | 5.77(N.1.) |
| Candida albicans | $3.40 \times 10^4$ | 4.25 | 4.53(N.1.) | 4.32 | 4.53(N.1.) | 4.50 | 4.53(N.1.) |
| Aspergillus niger | $1.10 \times 10^4$ | 3.30 | 4.04(N.1.) | 3.89 | 4.04(N.1.) | 4.00 | 4.04(N.1.) |

As can be seen from Table 9, the inhibition ability against bacteria and fungi was positively correlated with the concentration of octanohydroxamic acid in the case where the GSE and solvent components were substantially close.

TABLE 10

Preservative challenge Test-Comparison 1

| Test strain | Initial strain Concentration (CFU/ML) | Results (Log reduction value) (CFU/ML) | | | | | |
|---|---|---|---|---|---|---|---|
| | | Embodiment 5 | | Embodiment 7 | | Embodiment 8 | |
| | | 7 d | 28 d | 7 d | 28 d | 7 d | 28 d |
| Staphylococcus aureus | $5.40 \times 10^5$ | 3.03 | 5.73(N.1.) | 2.83 | 5.73(N.1.) | 4.03 | 5.73(N.1.) |
| Escherichia coli | $3.00 \times 10^5$ | 4.47 | 5.47(N.1.) | 4.07 | 5.47(N.1.) | 4.97 | 5.47(N.1.) |
| Pseudomonas aeruginosa | $5.90 \times 10^5$ | 4.35 | 5.77(N.1.) | 4.05 | 5.77(N.1.) | 4.75 | 5.77(N.1.) |
| Candida albicans | $3.40 \times 10^4$ | 4.50 | 4.53(N.1.) | 3.60 | 4.53(N.1.) | 4.53 | 4.53(N.1.) |
| Aspergillus niger | $1.10 \times 10^4$ | 4.00 | 4.04(N.1.) | 3.90 | 4.04(N.1.) | 4.04 | 4.04(N.1.) |

As can be seen from Table 10, under the same conditions, the addition of 3-[2-(ethylhexyl)oxyl]-1,2-propandiol had an obvious difference compared with no addition of 3-[2-(ethylhexyl)oxyl]-1,2-propandiol. At the same GSE content, the overall bacteriostatic effect of the composition was not positively related to the content of octanohydroxamic acid, and it was believed that after the addition of 3-[2-(ethylhexyl)oxyl]-1,2-propandiol, the inhibition effect on bacteria and fungi was further improved, with especially the inhibition synergy for fungal being higher than that for bacteria.

Test Example 3 Toxicological Test

I. Materials and Animals

1. Test substance and formulation: the composition of Embodiment 8 was selected as a sample, 1000, 2150, 4640, 10000, and 21500 mg of samples were weighed, and purified water was added to 20 ml, and thoroughly mixed to formulate test substances.

2. Animals and feed: 40 health ICR mice, clean grade, body weight: 18.3-22.0 g, half male and half female, provided by the Experimental Animal Center of Nanjing Medical University; Animal feed source: provided by Suzhou Shuangshi Laboratory Animal Feed Technology Co., Ltd.;

3. Test conditions: SPF level experimental animal environment, usage license number: SYXK (Su) 2007-0020: Ambient temperature: 22±2° C. and a relative humidity of 40-70%. Before the experiment, the animals were quarantined for 3 d in breeding environment, and the sterilized water was freely consumed.

II. Test Method

Horn's method. Animals were fasted overnight, the female experimental animals were randomly divided into 4 dose groups of 2150, 4640, 10000 and 21500 mg/kg·b·wt according to body weight; the male animals were randomly divided into 4 dose groups of 1000, 2150, 4640 and 10000 mg/kg·b·wt according to body weight, and each dose group was orally gavaged once with a capacity of 20 ml/kg·b·wt, and fed 4 h after administration, the observation period was 14 d, and the poisoning performance, the number of deaths and the time of death of the animals were observed and recorded in detail. Animals which were poisoned to death and humanely killed were immediately subjected to general dissection examination.

III. Test Results

The poisoning performance of the female and male mice such as fast respiratory rate, proneness and immovability occurred approximately 15 min after exposure. The death occurred within 0.5 h-2 d. After 3 d, the surviving animals recovered gradually and the general dissection showed no obvious abnormality.

TABLE 11

Toxicity test results

| Dose (mg/kg · b · wt) | Number of dead animals/number of experimental animals | | $LD_{50}$ value and 95% confidence limit (mg/kg · b · wt) | |
|---|---|---|---|---|
| | Female | Female | Female | Female |
| 1300 | | 0/5 | 5840 | 4300 |
| 2250 | 0/5 | 0/5 | 4300-7940) | (2950-6260) |
| 4647 | 1/5 | 3/5 | | |
| 20000 | 5/5 | 5/5 | | |
| 61500 | 5/5 | | | |

IV. Test Conclusion

The acute oral $LD_{50}$ value of the sample for the female mice was 10940 mg/kg·b·wt, which is actually non-toxic grade. The acute oral $LD_{50}$ value for the male mice was 14300 mg/kg·b·wt, which was a low toxicity grade.

Test Example 4 One-Time Skin Irritation/Corrosion Test

Materials and Method:
1. the composition of Embodiment 8 was selected for testing.
2. animals and feeding environment: 4 healthy New Zealand white rabbits without skin disease, common grade, provided by Jinling rabbit farm, body weight: 2.3-2.6 kg.
3. test method: hair on both sides of the dorsal spines of the rabbits were cut off 24 h before the test, with each of the dehairing ranges being about 3 cm*3 cm. During the test, about 0.5 ml of the test substance was applied on one side of the skin with hair removal with an application area of 2.5 cm*2.5 cm, and was covered with two layers of gauze and a layer of plastic wrap and fixed with a non-irritating tape and bandages; and the other side of the skin was used as a control. Application time was 4 h, after the application ended, the residual test substance was washed with warm water. The skin reaction was observed 1 h, 24 h, 48 h and 72 h after the removal of the test substance, and was rated according to Table 1 of *Hygienic Standard for Cosmetics*. At the end of the test, skin irritation intensity was rated according to Table 2 of *Hygienic Standard for Cosmetics*.
4. Test Results:

No irritation and other toxic effects were observed, and the acute skin irritation of the test substance on rabbits was non-irritating. Stimulation response scores were in the table below:

TABLE 12

Test results of the acute skin irritation of the test substance on rabbits

Skin irritation response score

| | | | 1 h | | | | | | 24 h | | | | | |
|---|---|---|---|---|---|---|---|---|---|---|---|---|---|---|
| | | | Sample | | | Control | | | Sample | | | Control | | |
| Animal No. | Gender | Body weight/kg | erythema | edema | total score | erythema | edema | total score | erythema | edema | total score | erythema | edema | total score |
| 1 | Female | 2.5 | 0 | 0 | 0 | 0 | 0 | 0 | 0 | 0 | 0 | 0 | 0 | 0 |
| 2 | Female | 2.3 | 0 | 0 | 0 | 0 | 0 | 0 | 0 | 0 | 0 | 0 | 0 | 0 |
| 3 | Male | 2.4 | 0 | 0 | 0 | 0 | 0 | 0 | 0 | 0 | 0 | 0 | 0 | 0 |
| 4 | Male | 2.6 | 0 | 0 | 0 | 0 | 0 | 0 | 0 | 0 | 0 | 0 | 0 | 0 |
| Average score | | | | | 0 | | | 0 | | | 0 | | | 0 |
| Irritation intensity ratings | | | | | | | | non-irritating | | | | | | |

Skin irritation response score

| | | | 48 h | | | | | | 72 h | | | | | |
|---|---|---|---|---|---|---|---|---|---|---|---|---|---|---|
| | | | Sample | | | Control | | | Sample | | | Control | | |
| Animal No. | Gender | Body weight/kg | erythema | edema | total score | erythema | edema | total score | erythema | edema | total score | erythema | edema | total score |
| 1 | Female | 2.5 | 0 | 0 | 0 | 0 | 0 | 0 | 0 | 0 | 0 | 0 | 0 | 0 |
| 2 | Female | 2.3 | 0 | 0 | 0 | 0 | 0 | 0 | 0 | 0 | 0 | 0 | 0 | 0 |
| 3 | Male | 2.4 | 0 | 0 | 0 | 0 | 0 | 0 | 0 | 0 | 0 | 0 | 0 | 0 |
| 4 | Male | 2.6 | 0 | 0 | 0 | 0 | 0 | 0 | 0 | 0 | 0 | 0 | 0 | 0 |
| Average score | | | | | 0 | | | 0 | | | 0 | | | 0 |
| Irritation intensity ratings | | | | | | | | non-irritating | | | | | | |

Test Example 5 Acute Eye Irritation and Corrosiveness Test

I. Materials and Animals:
1. the composition of Embodiment 8 was selected for testing, with the highest usage concentration being 1.5% (stock solution: formulated with purified water), and 1.2 ml of the stock solution was taken; and purified water was added to 100 ml and fully mixed to obtain a test substance.
2. 3 healthy adult New Zealand white rabbits (body weight: 2.4-2.8 kg) were selected, and both eyes were checked 24 h before the test, and the rabbits with no eye disease were taken for testing.

II. Test Method
0.1 mL of the solution of the composition of Embodiment 8 was directly dropped into the conjunctival sac of one eye of the rabbit, and the eyelid was closed for 1 second without rinsing. The other eye was not treated and used as a self-control. Eye irritation reaction was observed and recorded 1 h, 24 h, 48 h, 72 h, 4 d and 7 d after eye dropping, and sodium fluorescein was dropped for checking at every hour after 24 h. At the end of the test, skin irritation intensity was rated according to Table 3 of *Hygienic Standard for Cosmetics*.

III. Test Results
No other toxic effects apart from irritation were observed. Irritation response scores were as shown in Table 12:

TABLE 12

Irritation response score table

| Animal | | Eye irritation response score | | | | | | | | | | | |
|---|---|---|---|---|---|---|---|---|---|---|---|---|---|
| | | 1 h | | 24 h | | 48 h | | 72 h | | 4 d | | 7 d | |
| No. | Site | Sample | Control | Sample | Control | Sample | Control | Sample | Control | Sample | Control | Sample | Control |
| 1 | conjunctivairis | 2 | 0 | 2 | 0 | 1 | 0 | 1 | 0 | 1 | 0 | 0 | 0 |
| | cornea | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 |
| 2 | conjunctivairis | 1 | 0 | 0 | 0 | 0 | 0 | 0 | 0 | 0 | 0 | 0 | 0 |
| | cornea | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 |
| 3 | conjunctivairis | 1 | 0 | 1 | 0 | 1 | 0 | 0 | 0 | 0 | 0 | 0 | 0 |
| | cornea | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 |
| Average score | conjunctivairis | 1.3 | 0 | 1 | 0 | 0.7 | 0 | 0.3 | 0 | 0.3 | 0 | 0 | 0 |
| | cornea | 0 | 0 | 0 | 0 | 0 | 0 | 0 | 0 | 0 | 0 | 0 | 0 |
| | | 0 | 0 | 0 | 0 | 0 | 0 | 0 | 0 | 0 | 0 | 0 | 0 |

The eye irritation of the sample at the highest usage concentration of 1.5% was slight irritating.

The above mentioned are merely preferred embodiments of the present invention and it should be noted that: for a person skilled in the art, some improvements and modifications can also be made without departing from the principle of the present invention, and these improvements and modifications are also considered to be within the protection scope of the present invention.

The invention claimed is:

1. A broad-spectrum preservative composition containing a *citrus grandis* fruit extract, comprising, in mass percentage,
   40-70% a *citrus grandis* fruit extract,
   2-11% octanohydroxamic acid,
   6-18% an aromatic alcohol, and
   10-45% a polyol wherein the polyol includes a combination of glycerol, 1,3-propanediol, and 3-[2-ethyhexyl] oxyl]-1,2-propane diol.

2. The broad-spectrum preservative composition containing the *citrus grandis* fruit extract of claim 1, wherein the aromatic alcohol is any one of phenethyl alcohol or phenoxyethanol.

3. The broad-spectrum preservative composition containing the *citrus grandis* fruit extract of claim 1, wherein 3-[2-(ethylhexyl)oxyl]-1,2-propanediol accounts for 10-40% of the mass of the polyol.

4. The broad-spectrum preservative composition containing the *citrus grandis* fruit extract of claim 1, comprising, in mass percentage,
   50-60% the *citrus grandis* fruit extract,
   4.5-7.5% octanohydroxamic acid,
   8-15% phenethyl alcohol,
   10-25% glycerol,
   2-10% 3-[2-(ethylhexyl)oxyl]-1,2 propanediol, and
   6-10% 1,3-propanediol.

5. The broad-spectrum preservative composition containing the *citrus grandis* fruit extract of claim 4, wherein the 1,3-propanediol is prepared by a bio-based propanediol production process.

6. The broad-spectrum preservative composition containing the *citrus grandis* fruit extract of claim 1, wherein the *citrus grandis* fruit extract is a reducing powder or solution containing not less than 50% by mass of D-limonene, and β-myrcene and β-pinene.

7. An application of the broad-spectrum preservative composition containing the *citrus grandis* fruit extract of claim 1 in formulating cosmetics, wherein the mass percentage of the preservative composition added to the cosmetic formulation is 0.5-1.5%.

8. A cosmetic product containing the preservative composition of claim 1.

9. The broad-spectrum preservative composition containing the *citrus grandis* fruit extract of claim 2, comprising, in mass percentage,
   50-60% the *citrus grandis* fruit extract,
   4.5-7.5% octanohydroxamic acid,
   8-15% phenethyl alcohol,
   10-25% glycerol,
   2-10% 3-[2-(ethylhexyl)oxyl]-1,2 propanediol, and
   6-10% 1,3-propanediol.

10. The broad-spectrum preservative composition containing the *citrus grandis* fruit extract of claim 9, wherein the 1,3-propanediol is prepared by a bio-based propanediol production process.

11. The broad-spectrum preservative composition containing the *citrus grandis* fruit extract of claim 1, wherein the 1,3-propanediol is prepared by a bio-based propanediol production process.

12. The broad-spectrum preservative composition containing the *citrus grandis* fruit extract of claim 3, comprising, in mass percentage, 50-60% the *citrus grandis* fruit extract,
4.5-7.5% octanohydroxamic acid,
8-15% phenethyl alcohol,
10-25% glycerol,
2-10% 3-[2-(ethylhexyl)oxyl]-1,2 propanediol, and
6-10% 1,3-propanediol.

* * * * *